(12) United States Patent
Zhao et al.

(10) Patent No.: US 10,615,399 B2
(45) Date of Patent: *Apr. 7, 2020

(54) POWER TERMINAL FOR IMPLANTABLE DEVICES

(71) Applicant: Medtronic, Inc., Minneapolis, MN (US)

(72) Inventors: Hailiang Zhao, Maple Grove, MN (US); Erik J. Hovland, Minnetonka, MN (US)

(73) Assignee: Medtronic Inc., Minneapolis, MN (US)

( * ) Notice: Subject to any disclaimer, the term of this patent is extended or adjusted under 35 U.S.C. 154(b) by 314 days.

This patent is subject to a terminal disclaimer.

(21) Appl. No.: 15/666,802

(22) Filed: Aug. 2, 2017

(65) Prior Publication Data
US 2017/0331099 A1    Nov. 16, 2017

Related U.S. Application Data

(63) Continuation of application No. 15/004,204, filed on Jan. 22, 2016, now Pat. No. 9,741,993.

(51) Int. Cl.
| | |
|---|---|
| *H01M 2/30* | (2006.01) |
| *A61N 1/378* | (2006.01) |
| *H01M 2/10* | (2006.01) |
| *H01M 2/26* | (2006.01) |
| *H01G 9/008* | (2006.01) |
| *H01G 9/048* | (2006.01) |
| *A61N 1/375* | (2006.01) |

(52) U.S. Cl.
CPC .............. *H01M 2/30* (2013.01); *A61N 1/375* (2013.01); *A61N 1/378* (2013.01); *H01G 9/008* (2013.01); *H01G 9/048* (2013.01); *H01M 2/1022* (2013.01); *H01M 2/26* (2013.01); *H01M 2/266* (2013.01); *H01M 2220/30* (2013.01)

(58) Field of Classification Search
CPC .......... H01M 2/266; H01M 2/30; H01M 2/26; H01M 2/1022; H01M 2220/30; H01G 9/048; H01G 9/008; A61N 1/378; A61N 1/375

See application file for complete search history.

(56) References Cited

U.S. PATENT DOCUMENTS

| | | |
|---|---|---|
| 9,741,993 B1 | 8/2017 | Zhao et al. |
| 2003/0091893 A1 | 5/2003 | Kishiyama et al. |

(Continued)

FOREIGN PATENT DOCUMENTS

| | | |
|---|---|---|
| EP | 0237146 A1 | 9/1987 |
| WO | WO 2012/057854 A1 | 5/2012 |

OTHER PUBLICATIONS

International Search Report and Written Opinion dated Jan. 30, 2017, for International Application No. PCT/US2016/062512, 12 pgs.

*Primary Examiner* — Michael W Kahelin
(74) *Attorney, Agent, or Firm* — Mueting, Raasch and Gebhardt, P.A.

(57) ABSTRACT

A battery terminal for an implantable battery is described. The battery terminal includes a foil stack, first and second side elements, and a weld joint coupling the foil stack and the side elements. The side elements define a varying height profile and a greatest height adjacent an inner surface of the side element in contact with the foil stack. Each element may define a height profile along the width that tapers toward an outer surface, biasing mass of the element close to the foil stack.

20 Claims, 9 Drawing Sheets

(56) References Cited

U.S. PATENT DOCUMENTS

2004/0127952 A1    7/2004   O'Phelan et al.
2007/0233195 A1   10/2007   Wahlstrand et al.
2013/0131745 A1    5/2013   Viavattine
2013/0302654 A1   11/2013   Schaefer
2015/0297898 A1   10/2015   Yakovlev et al.

POWER TERMINAL FOR IMPLANTABLE DEVICES

CROSS-REFERENCE TO RELATED APPLICATION

This is a continuation application of U.S. patent application Ser. No. 15/004,204 filed Jan. 22, 2016, the disclosure of which is incorporated by reference herein in its entirety.

BACKGROUND

Implantable electrical signal generators, such as pacemakers, defibrillators, neurostimulators, and the like, have been used to treat a variety of diseases. Such devices generate electrical signals that are transferred to a patient's tissue through electrodes present on a distal end portion of a lead. Many devices include stimulation electronics coupled to an electrical power supply, such as a battery. In many cases, the power supply is electromechanically coupled to the stimulation electronics with a robust connection suitable for providing the power required by the stimulation electronics. In some cases, the connection is formed by welding at a power terminal. However, various power supplies include components that are susceptible to melting at high welding temperatures, such as separators between plate electrodes in a rechargeable battery. Accordingly, forming a robust electromechanical connection at a power terminal presents particular challenges.

SUMMARY

The present disclosure relates to interconnects for power supplies. In particular, a power terminal facilitates a robust electrical connection between an internal power source in a power supply and conductor pins extending from the power supply for reliable power delivery from the power source.

In one illustrative embodiment, a battery terminal includes a foil stack, a first side element, a second side element, and a weld joint. The foil stack includes a plurality of free end portions of foil tabs stacked along a stacking direction and electrically coupled to a plurality of plate electrodes. The foil stack defines a free end side, a first stack surface, a second stack surface opposite the first stack surface, and a foil stack width along the stacking direction between the first stack surface and the second stack surface. The first side element defines a first inner surface, a first outer surface opposite the first inner surface, a first width between the first inner and outer surfaces, and a first height profile varying along the first width between a top and a bottom of the first side element. The first inner surface is coupled to the first stack surface. The first height profile defines a greatest height of the first side element adjacent the first inner surface. The second side element defines a second inner surface, a second outer surface opposing the second inner surface, a second width between the second inner and outer surfaces, and a second height profile varying along the second width between a top and a bottom of the second side element. The second inner surface is coupled to the second stack surface. The second height profile defines a greatest height of the second side element adjacent the second inner surface. The weld joint is at the free end side of the foil stack coupling the plurality of free end portions, the first side element, and the second side element.

In another illustrative embodiment, a battery includes a plate electrode stack, a plurality of cathode foil tabs, a plurality of anode foil tabs, and battery terminals. The plate electrode stack includes a plurality of alternating cathode and anode plate electrodes each bagged in a separator. The plurality of cathode foil tabs are electrically coupled to the plurality of alternating cathode plate electrodes. The plurality of anode foil tabs are electrically coupled to the plurality of alternating anode plate electrodes. The battery terminals include a cathode terminal electrically coupled to the plurality of cathode foil tabs and an anode terminal electrically coupled to the plurality of anode foil tabs. Each battery terminal includes a foil stack, a first side element, a second side element, and a weld joint. The foil stack includes a plurality of free end portions of foil tabs stacked along a stacking direction and electrically coupled to a plurality of plate electrodes. The foil stack defines a free end side, a first stack surface, a second stack surface opposite the first stack surface, and a foil stack width along the stacking direction between the first stack surface and the second stack surface. The first side element defines a first inner surface, a first outer surface opposite the first inner surface, a first width between the first inner and outer surfaces, and a first height profile varying along the first width between a top and a bottom of the first side element. The first inner surface is coupled to the first stack surface. The first height profile defines a greatest height of the first side element adjacent the first inner surface. The second side element defines a second inner surface, a second outer surface opposing the second inner surface, a second width between the second inner and outer surfaces, and a second height profile varying along the second width between a top and a bottom of the second side element. The second inner surface is coupled to the second stack surface. The second height profile defines a greatest height of the second side element adjacent the second inner surface. The weld joint is at the free end side of the foil stack coupling the plurality of free end portions, the first side element, and the second side element.

In a further illustrative embodiment, an implantable medical device includes stimulation electronics and a battery operatively coupled to the stimulator to power the stimulation electronics. The battery includes one or more of a foil stack, a first side element, a second side element, and a weld joint. The foil stack includes a plurality of free end portions of foil tabs stacked along a stacking direction and electrically coupled to a plurality of plate electrodes. The foil stack defines a free end side, a first stack surface, a second stack surface opposite the first stack surface, and a foil stack width along the stacking direction between the first stack surface and the second stack surface. The first side element defines a first inner surface, a first outer surface opposite the first inner surface, a first width between the first inner and outer surfaces, and a first height profile varying along the first width between a top and a bottom of the first side element. The first inner surface is coupled to the first stack surface. The first height profile defines a greatest height of the first side element adjacent the first inner surface. The second side element defines a second inner surface, a second outer surface opposing the second inner surface, a second width between the second inner and outer surfaces, and a second height profile varying along the second width between a top and a bottom of the second side element. The second inner surface is coupled to the second stack surface. The second height profile defines a greatest height of the second side element adjacent the second inner surface. The weld joint at the free end side of the foil stack couples the plurality of free end portions, the first side element, and the second side element.

These and various other features and advantages will be apparent from a reading of the following detailed description.

BRIEF DESCRIPTION OF THE DRAWINGS

The disclosure may be more completely understood in consideration of the following detailed description of various embodiments of the disclosure in connection with the accompanying drawings.

DETAILED DESCRIPTION

Figure 1:
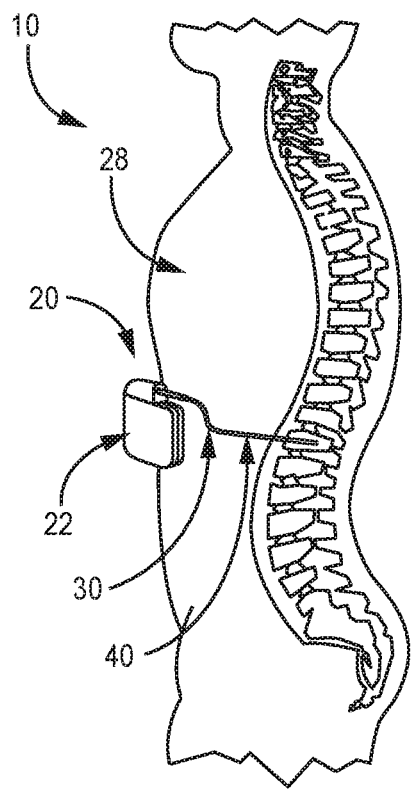
FIG. 1 is a diagrammatic representation of a general environmental view for a neurostimulation system embodiment.

In the following detailed description, reference is made to the accompanying drawings that form a part hereof, and in which are shown by way of illustration several specific embodiments. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising," and the like.

The term "coupled" refers to two elements being attached to each other either directly (in direct contact with each other) or indirectly (having one or more elements between and attaching the two elements).

Terms related to orientation, such as "top", "bottom", "side", and "end", are used to describe relative positions of components and are not meant to limit the orientation of the embodiments contemplated. For example, an embodiment described as having a "top" and "bottom" also encompasses embodiments thereof rotated in various directions unless the content clearly dictates otherwise.

The present disclosure relates to an interconnect in a power supply. The interconnect facilitates a robust electrical connection between an internal power source in the power supply and pins extending from the power supply for reliable power delivery from the power source. The interconnect may include one or more conductors electrically coupled to the internal power source, one or more elements for mechanical rigidity, and a weld joint for coupling thereof. The interconnect may form a power terminal, to which a pin of the power supply may be welded for external electrical coupling. In one embodiment, the one or more conductors are foil tabs, and each element compresses the foil tabs into a foil stack. The elements may be coupled to a portion of the foil stack by a weld joint. In some embodiments, each element defines a varying height profile and a greatest height adjacent the inner surface. In many embodiments, each element defines a height profile along the width that tapers toward an outer surface, biasing mass of the element close to the conductors for efficient welding, for example, to reduce welding energy requirements, and formation a robust electromechanical joint. Reduced welding energy mitigates risks associated with damaging components in close proximity susceptible to melting at high temperatures. In further embodiments, the entire length of a conductor is coupled to the element inner surface to increase contact, thereby facilitating a reliable electrical connection and power throughput. While the present disclosure is not so limited, an appreciation of various aspects of the disclosure will be gained through a discussion of the examples provided below.

FIG. 1 shows a general environmental view 10 for an implantable stimulation system. While a stimulation system is illustrated, it is understood that any implantable medical device having a lead body may be utilized with the filer connection and methods described herein.

Stimulation system 20 includes a stimulator 22 (such as a neurostimulator, for example), an optional stimulation lead extension 30, and a stimulation lead 40. Stimulator 22 is typically implanted subcutaneously in a patient's body 28 at a location selected by the clinician; although FIG. 1 illustrates stimulator 22 implanted in the patient's abdomen, other locations are suitable. Stimulation lead 40 is typically fixed in place terminating near the desired location selected by the clinician using a device such as an adjustable anchor.

Figure 2:
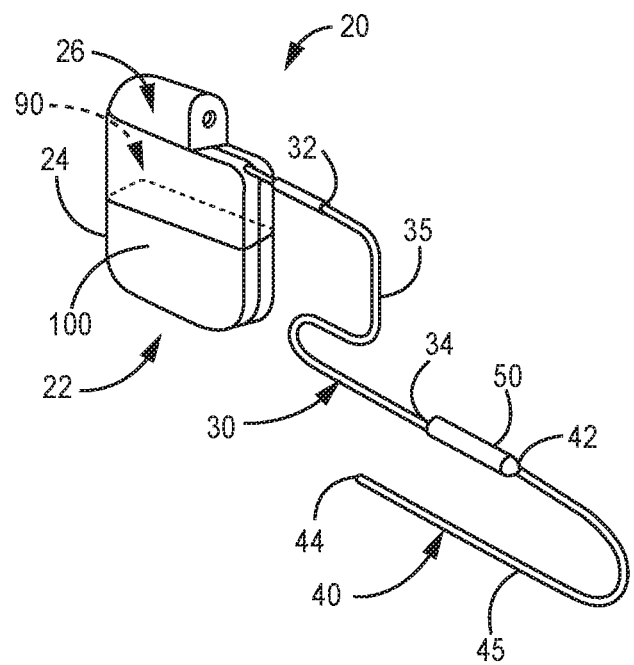
FIG. 2 is a perspective view of the illustrative neurostimulation system of FIG. 1.

FIG. 2 shows an enlarged view of implantable stimulation system 20 having implantable stimulator 22, stimulation lead 40, and optional lead extension 30. Implantable stimulator 22 has a housing 24, a power supply 100, and stimulation electronics 90 within the housing 24 coupled to the power supply and coupled to a connector block 26, which is also known as a terminal block.

In the embodiment shown, the power supply 100 includes a portion of the housing 24 and may be exposed to the environment 10 (FIG. 1). In many embodiments, the power supply 100 is a battery capable of powering the stimulation electronics 90. Although other forms of supplying power are contemplated, herein throughout, the power supply 100 is referred to as a battery 100 to provide a concise description of an example power supply. In one embodiment, the battery 100 is a rechargeable battery including a plate electrode stack.

Stimulation lead 40 has a lead proximal end 42, a lead distal end 44 and a lead body 45. At lead distal end 44 is medical device such as an electrode contact having at least one stimulation electrode (not illustrated). Lead extension 30 has an extension proximal end 32, an extension distal end 34, and an extension body 35. Lead proximal end 42 connects to lead extension distal end 34 at connector 50; either or both lead proximal end 42 or extension distal end 34 may include an electrode tip that engages with connector 50.

Lead 40 and lead extension 30 provide electrical communication from stimulator 22 to the electrode contact at distal end 44. Lead distal end 44 contains at least one electrode but in most embodiments has a plurality of such electrodes (e.g., 4, 8, 16, etc.). Extending through lead 40 and lead extension 30 are electrically conducting wire, often referred to as filars or wire filars, that couple stimulator 22 to the electrode contact and its electrode(s). Extending over and covering the wire filars is an electrically insulating jacket or sheath. In some embodiments, a shielding layer or jacket may be present, optionally over the insulating jacket.

The present disclosure is directed to a battery terminal in the battery 100 including side elements electrically coupled between an internal electrochemical power source and battery pins. The battery terminal may be used in any suitable battery 100, such as a rechargeable plate electrode battery including separators, which may be susceptible to the high temperatures of welding. The battery terminal provides a robust electromechanical connection for the reliable charging and delivery of power to the stimulation electronics 90 in the stimulator 22. Furthermore, the battery terminal facilitates the miniaturization of the battery 100 and therefore miniaturization of the stimulator 22, as well, for ease of use as an implantable device. It should be understood that the following discussion of the side elements of this invention makes reference to the terminals of a battery, and the like, generically, and that this discussion is not limiting to positions or uses of the side elements in this disclosure, but that the side elements may be used in any electromechanical connection in the stimulator. It should also be understood that the side elements could be used with applications other than just stimulators.

Figure 3:
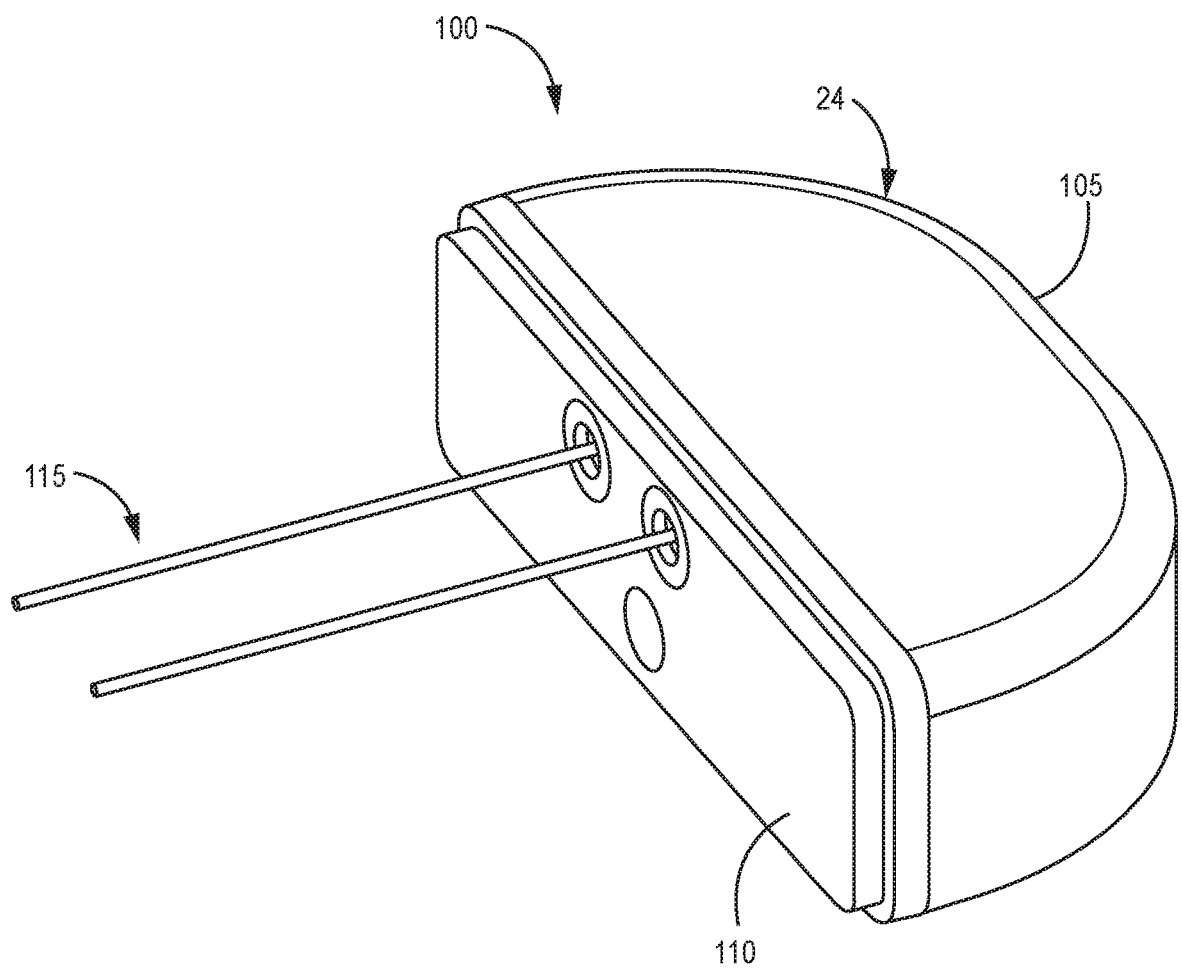
FIG. 3 is an assembled, perspective view of an illustrative power supply of FIG. 1 in the form of a battery.
Figure 4:
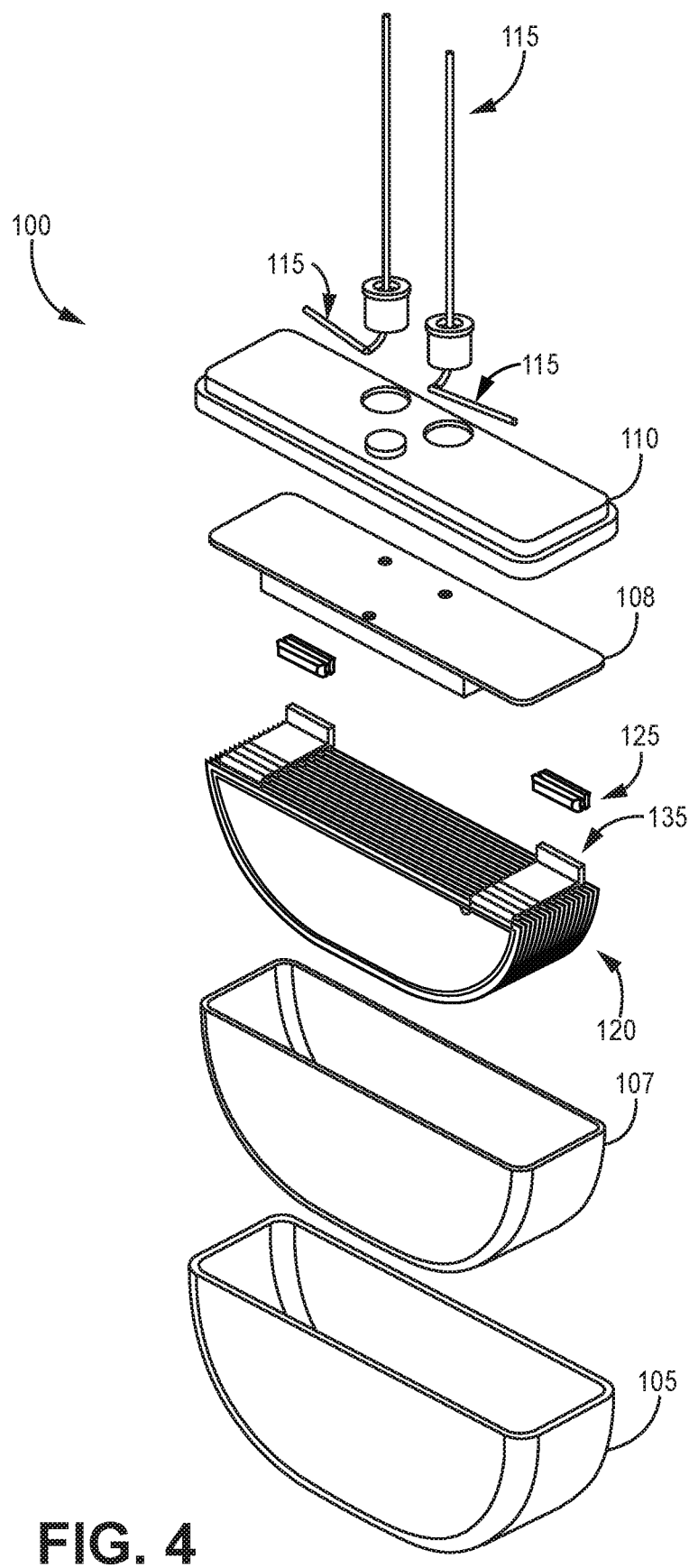
FIG. 4 is a exploded, perspective view of the illustrative battery of FIG. 3.

Referring to FIGS. 3 and 4, an illustrative power supply in the form of a battery 100 is shown as an assembled, perspective view in FIG. 3 and as an exploded, perspective view in FIG. 4. The battery 100 may form a part of the exterior of the stimulator 22. As shown, the battery includes housing portion 105 of the housing 24 and battery cap 110. The housing portion 105 may be smooth and rounded to facilitate implantation. The battery cap 110 may be welded and sealed to another portion of the housing 24 to isolate a set of battery pins 115 from an environment external to an implantable device.

The illustrative battery 100 may be charged to store electrochemical energy and may deliver the stored energy selectively to an external device through the battery pins 115 extending through the battery cap 110 and outward from the battery. The battery pins 115 may be potted in the battery cap 110 to further seal the battery 100 from an environment internal to the implantable device, for example, to protect the battery chemistry from contaminants. The battery may include other components not discussed herein in detail, such as a liner.

Perhaps as best shown in FIG. 4, each illustrative battery pin 115 is shown including an external portion extending from the battery cap 110 and an internal portion connected to the external portion (e.g., one integral body) extending into the battery 100 when assembled. The battery pins 115 are configured to transfer power into and out of the battery 100.

The battery 100 may further include an internal power source (e.g., plate electrode stack 120), one or more supporting elements (e.g., side elements 125), and one or more conductors (e.g., foil tabs 135). In the illustrated embodiment, the battery 100 includes an illustrative plate electrode stack 120 as the power source. The illustrative plate electrode stack 120 is disposed internally between the housing portion 105 and the battery cap 110 and may serve as a power source for receiving, storing, and delivering electrochemical energy. In many embodiments, the plate electrode stack 120 includes a plurality of plate electrodes. The plate electrode stack 120 may also have a complementary shape to be received by the housing portion 105 and to maximize energy storage volume therein. The battery 100 may also include an insulating liner 107 and liner cap 108.

As illustrated, the battery 100 includes four illustrative side elements 125 (two for each terminal) as the supporting elements, for example. The side elements 125 may be disposed between the plate electrode stack 120 and the battery cap 110 and may serve as rigid mechanical supports for the conductors (e.g., foil tabs 135). Furthermore, each side element 125 may serve as a structure disposed between a conductor (e.g., foil tabs 135) and a battery pin 115 for coupling the battery pin 115 thereto, for example, to electrically couple the battery pin to the conductor 135.

Also, as shown, the battery 100 includes two sets of illustrative foil tabs 135 (one anode and one cathode) as conductors, for example. The foil tabs 135 may be disposed between the plate electrode stack 120 and the battery pins 115 and may serve as electrical conductors there between. Each set of foil tabs 135 may include a plurality of foil tabs, each connected to a plate electrode in the stack.

Figure 5:
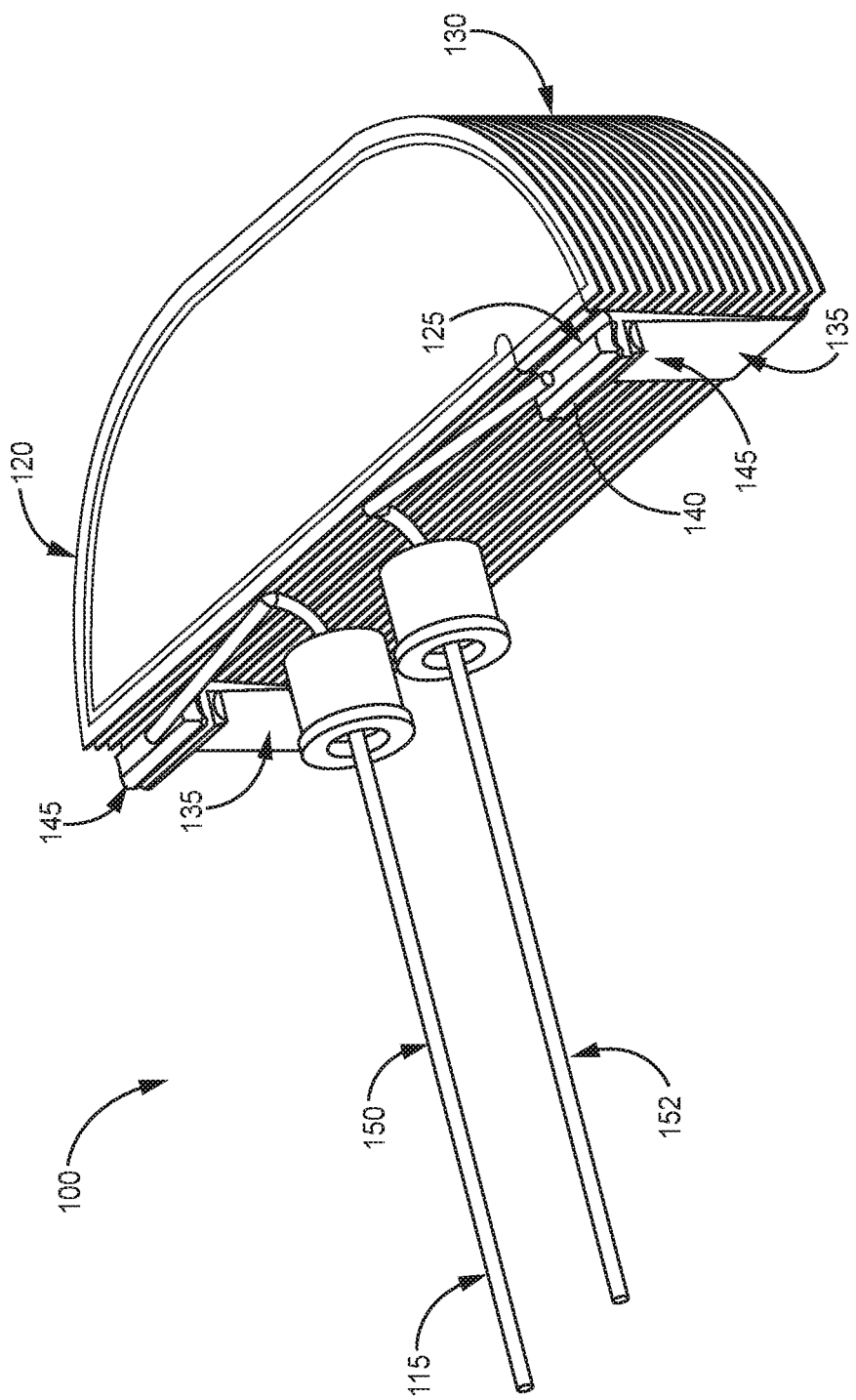
FIG. 5 is a partially-assembled, perspective view of the illustrative battery of FIG. 3.
Figure 6:
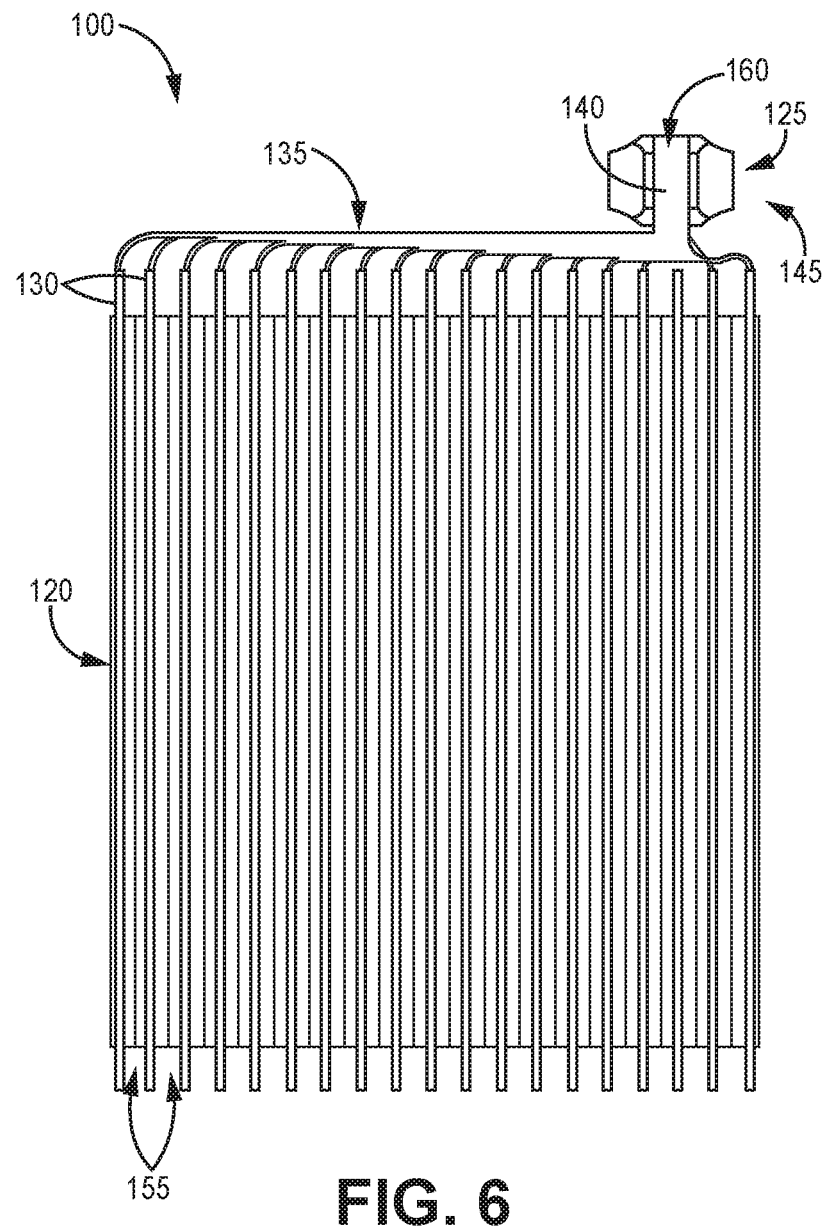
FIG. 6 is a partially-assembled, elevation view of the illustrative battery of FIG. 3 showing an illustrative battery terminal.

FIGS. 5 and 6 show partially-assembled views of the illustrative battery 100. FIG. 5 is a partially-assembled, perspective view of the illustrative battery 100 showing the electrical pathway through the battery 100. FIG. 6 is a partially-assembled, elevation view of the illustrative battery 100 showing the plate electrode stack 120 and an illustrative battery terminal 145 portion of the electrical pathway.

An illustrative electrical pathway includes a first end at a battery pin 115, a side element 125, a set of foil tabs 135, and a second end at the plate electrode stack 120. The components in the electrical pathway may be coupled by any suitable means. In many embodiments, the components are coupled by welding. Any suitable method for welding may be utilized, such as resistance welding or fusion welding, such as laser beam welding, electrical arc welding, or plasma welding, for example. In one example, a set of foil tabs 135 and a pair of side elements 125 are coupled by laser beam welding. In another example, the battery pin 115 is coupled to a side element 125 by resistance welding.

The plate electrode stack 120 may include a plurality of plate electrodes 130. As shown, the plate electrodes 130 are stacked along a stacking direction with a major surface of one plate electrode adjacent a major surface of another plate electrode.

Each of the plate electrodes 130 may be individually bagged in an insulator (e.g., separator 155) to electrically isolate each plate electrode. In many embodiments, the insulator is an inert (e.g., inactive) porous polymeric separator 155, which electrically insulates adjacent plate electrodes while allowing the flow of ions in the electrolyte. In many cases, the separator 155 is susceptible to melting at high temperatures. For example, the separator 155 may melt at as low as 120 degrees Celsius or as low as 165 degrees Celsius, for example. The heat generated during laser beam welding may achieve or exceed such melting temperatures and thus may damage the separator.

The illustrative battery 100 defines two sets of plate electrodes 130 electrically coupled by conductors. In many embodiments, one set of plate electrodes 130 is coupled to one set of foil tabs 135 and another set of plate electrodes 130 is coupled to another set of foil tabs 135. Each set of the plate electrodes 130 may serve as either a cathode or an anode of the battery 100. In the illustrated embodiment, the plate electrode stack 120 is formed from a plurality of alternating cathode and anode plate electrodes 130, each bagged in a separator 155, and each electrically coupled to a respective foil tab 135.

In the illustrated embodiment, each set of foil tabs 135 include an end that fans out and a free end portion 160 that forms a foil stack 140. Each foil tab 135 at the fanned out end may electrically couple to a corresponding plate electrode 130. Each foil tab 135 at the free end portion 160 may electrically couple to the surface of another foil tab at the corresponding free end portion. Hence, each set of foil tabs 135 electrically couples a set of plate electrodes 130 together, such as the set of cathode plate electrodes or the set of anode plate electrodes. As illustrated, two sets of foil tabs 135 form two foil stacks 140 including the corresponding free end portions 160.

In various embodiments, the foil tabs 135 are formed and sized to transfer electrical energy in a miniature battery 100 for an implantable device. In one embodiment, an exemplary foil tab 135 has a thickness of about 20 microns (micrometers). When assembled, the exemplary foil tabs 135 are stacked along a stacking direction to form a foil stack 140 with the free end portions 160 of the foil tabs 135. However, other thicknesses suitable for various applications are also contemplated, for example, based on physical and electrical properties. Each foil tab 135 may be formed of any suitable conductive material malleable into a tab or strip, such as a metal like aluminum, for example.

Each foil stack 140 may be coupled to one or more side elements 125, which serve to join the foil tabs 135 together. In many embodiments, the side elements 125 facilitate compression of the foil tabs 135 in the foil stack 140 to remove gaps between the foil tabs and providing a rigid mechanical support to the foil stack 140, thereby facilitating a robust electrical coupling among the foil tabs. In the illustrated embodiment, each foil stack 140 is flanked by a first side element 125 and a second side element 125 opposite the first side element to compress the foil stack between the side elements.

In various embodiments, the battery 100 defines two electrical pathways, a cathode circuit 150 and an anode circuit 152, coupled by battery chemistry to complete an electrical circuit. In one embodiment, the cathode circuit 150 may include a cathode pin 115, a cathode side element 125, a set of cathode foil tabs 135, and a set of cathode plate electrodes 130. In one embodiment, the anode circuit 152 may include an anode pin 115, an anode side element 125, a set of anode foil tabs 135, and a set of anode plate electrodes 130. The cathode circuit 150 and the anode circuit 152 may be electrochemically coupled by the flow of ions in the electrolyte inside the battery and the flow of electrons outside of the battery between the cathode and anode plate electrodes 130 when the battery 100 in use, thereby joining the cathode and anode pins 115 in one electrical circuit of the battery.

The battery 100 may further define one or more battery terminals 145. Each battery terminal 145 may include a side element 125 and a foil stack 140. As illustrated, two battery terminals 145 include a cathode battery terminal and an anode battery terminal along the respective cathode or anode circuit 150, 152, each including two side elements 125 and a foil stack 140.

In many embodiments, a battery pin 115 is welded to one side element 125 of the battery terminal 145. Because the side elements 125 space apart the foil stack 140 from the battery pins 115, the side elements may also be described as spacers 125 herein.

Figure 7:
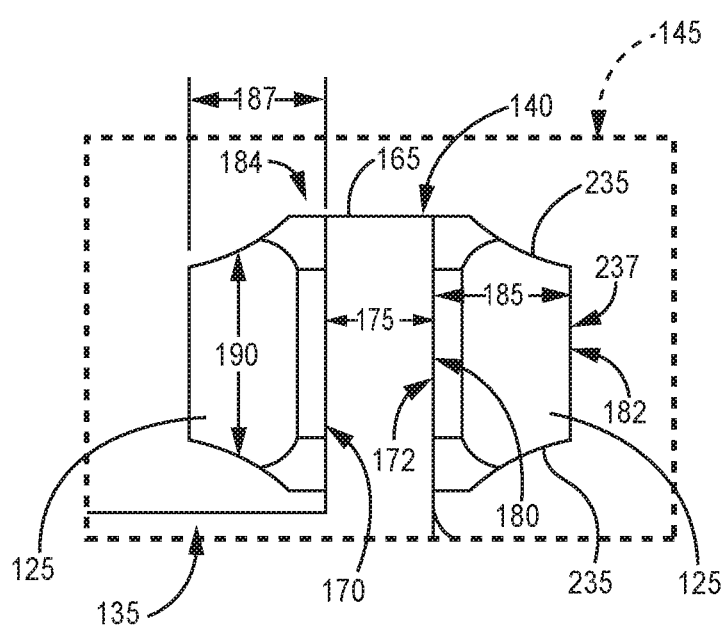
FIG. 7 is one side elevation view of the illustrative battery terminal of FIG. 6 showing illustrative side elements in the form of a spacer.
Figure 8:
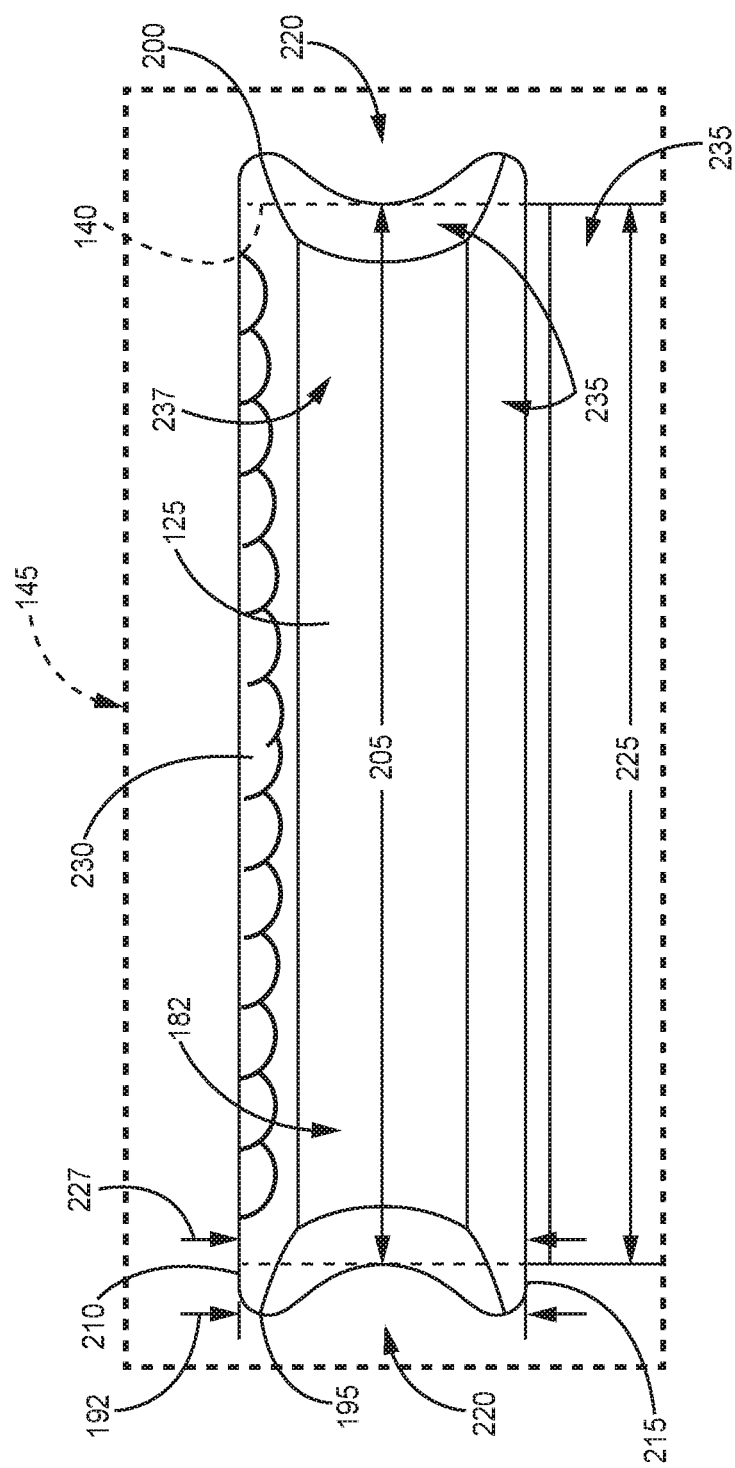
FIG. 8 is another side elevation view of the illustrative battery terminal of FIG. 6 showing illustrative side elements in the form of a spacer.
Figure 9:
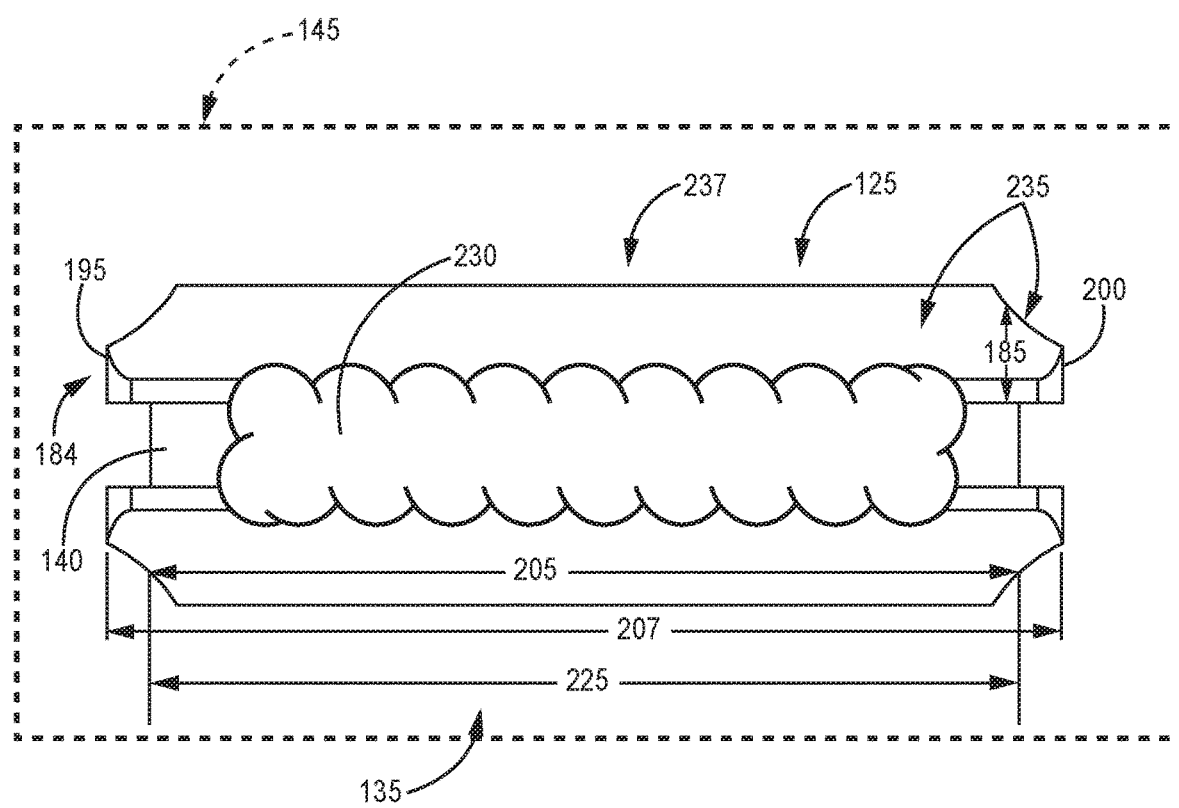
FIG. 9 is a top view of the illustrative battery terminal of FIG. 6 showing illustrative side elements in the form of a spacer.
Figure 10:
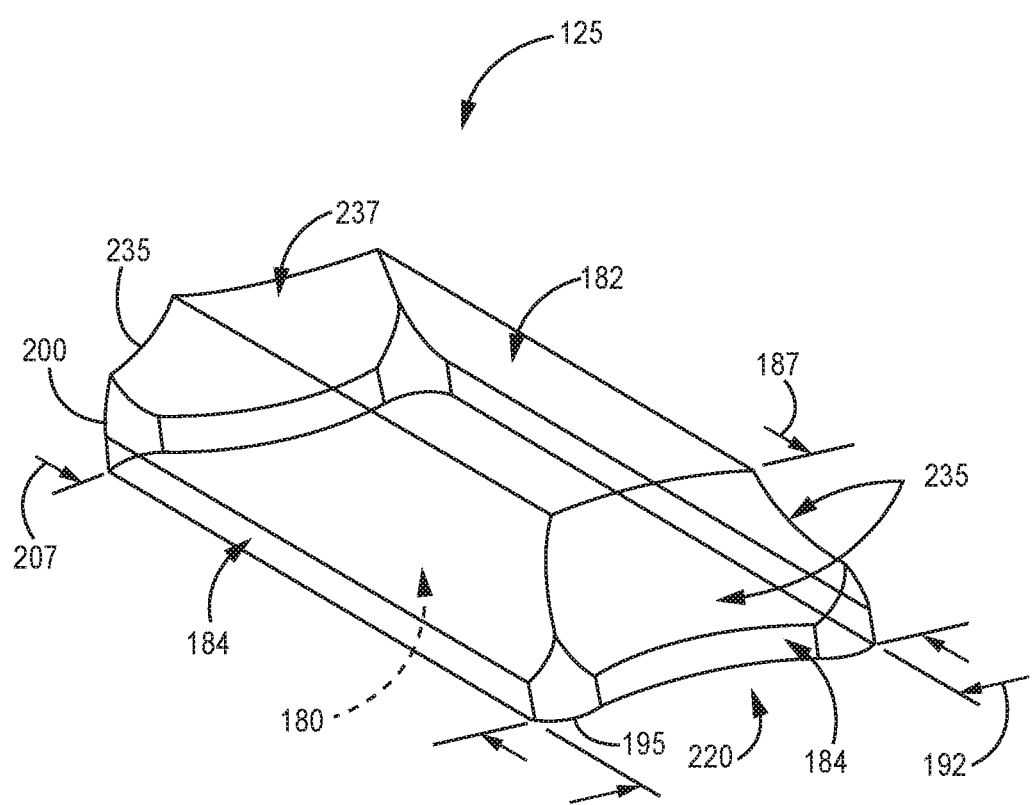
FIG. 10 is a perspective view of an illustrative side element in the form of a spacer of FIGS. 7-9.

FIGS. 7-10 show an illustrative battery terminal 145 and side element in the form of a spacer 125. In particular, FIG. 7 is a side elevation end-view, FIG. 8 is a side elevation major surface-view, and FIG. 9 is a top view of the illustrative battery terminal 145 including illustrative spacers 125 disposed adjacent a free end side 165 of the foil stack 140. FIG. 10 is a perspective transparent-view of the illustrative spacer 125.

The spacer 125 defines an inner surface 180, an outer surface 182 opposite the inner surface, and one or more side surfaces 184 extending between the inner and outer surfaces. In one embodiment, the spacer 125 is in the shape of a trapezoidal prism, generally.

In various embodiments, the spacer 125 is formed of titanium or aluminum. In one embodiment, the spacer 125 is formed of grade 5 titanium. In another embodiment, the spacer 125 is formed of grade 23 titanium.

In many embodiments, the shape of the spacer 125 is formed by an etching process. An exemplary etching process, begins with a sheet of spacer material (e.g., titanium) having a first surface and an opposing second surfaces. The sheet may then be etched from the first surface to form the desired shape for the spacer 125. In particular, the etching process defines the contours of the tapered portions 235 and associated width, height, and length profiles. In many embodiments, the etching process results in a concave, curved taper and a greatest height and width of the spacer 125 adjacent the second surface of the spacer, in contrast to conventional etching processes for titanium involving etching from both sides wherein the greatest height and width are formed between the surfaces (e.g., the sides represent ridges with peaks halfway between the surfaces).

As shown, the inner surface 180 is substantially flat to facilitate surface area contact. Furthermore, the inner surface 180 may define a generally rectangular shape with rounded corners.

The outer surface 182 may define one or more tapered portions 235 and non-tapered portions 237. Tapered portions 235 may extend between the non-tapered portion 237 and each side portion 184. In many embodiments, the tapered portions 235 define curved tapers. In the illustrated embodiment, the curved tapers are concave.

The spacer 125 also extends from a first end portion 195 to a second end portion 200. The spacer 125 further extends from a top end portion 210 to a bottom end portion 215. Each end portion 195, 200, 210, 215 may include a side surface 184 and a tapered portion 235 of the outer surface 182. In various embodiments, the tapered portions 235 are etched back from one or more ends portions 195, 200, 210, 215 by a distance of more than about 5 mils (thousands of an inch) or about 1 mil along the outer surface 182 (e.g., about 130 microns or about 25 microns, respectively). In many embodiments, the etch-back distance is less than 10 mils to maintain structural integrity and to provide sufficient mass for welding the spacer as needed.

The illustrative spacer 125 defines a width 185 extending from the inner surface 180 to the outer surface 182. The illustrative spacer 125 also defines a length 205 between the first and second end portions orthogonal to the width 185. The illustrative spacer 125 further defines a height 190 between the top and bottom end portions orthogonal to the width 185 and the length 205.

In many embodiments, the width 185 has a variable profile. For example, the illustrative width 185 varies between the inner surface 180 and the tapered portion 235 of the outer surface 182 along the height 190 or length 205. The width 185 may also define a greatest width 187. As shown, the greatest width 187 is between the inner surface 180 and the non-tapered portion 237 of the outer surface 182. In various embodiments, the greatest width 187 is about 10 mils (about 254 microns).

In a similar manner, the height 190 may also have a variable profile. For example, the illustrative height 190 varies between the tapered portions 235 of the first and second end portions 195, 200. As shown, the height 190 may also define a greatest height 192 between the side surfaces 184 of the end portions 210, 215. In many embodiments, the greatest height 192 is adjacent the inner surface 180. In various embodiments, the greatest height 192 is about 20 mils (about 508 microns). In some embodiments, the non-tapered portions 237 of the outer surface 182 define a height 190 ranging from about 8 mils (about 200 microns) to about 12 mils (about 305 microns).

Together, the illustrative variable profiles of the width 185 and height 190 define a symmetrical, generally trapezoidal cross-sectional shape (see FIG. 7). The generally trapezoidal shape may include a concave edge defined by the tapered portions 235 of the outer surface 182.

In the illustrated embodiment, the spacer 125 includes a recess 220 defining at least part of the variable profile of the length 205. In many embodiments, the illustrative length 205 defines a greatest length 207 adjacent the top and/or bottom end portions 210, 215 and varies between those ends varies along the width 185 or the height 190 to form the recess 220 including a minimum length. The recess 220 may be useful, for example, to align the spacers 125 and the foil stack 140 between two assembly pins prior to welding with each pin being nestled by a corresponding recess. In various embodiments, the greatest length 207 is more than about 70 mils, less than about 90 mils (about 2290 microns), about 75 mils (about 1900 microns), or about 82 mils (about 2080 microns).

As shown, the foil stack is positioned between two spacers 125. The foil stack 140 defines a first stack surface 170 and a second stack surface 172 opposite the first stack surface. In some embodiments, the surfaces 170, 172 each correspond to a surface of a foil tab 135 at the ends of the foil stack 140.

The foil stack 140 also defines a foil stack width 175 along the stacking direction, a foil stack length 225 orthogonal to the width, and a foil stack height 227 orthogonal to the width and length. As illustrated, the width 175 is defined between the first stack surface 170 and the second stack surface 172. The length 225 may be the same as the length of the set of foil tabs 135 and similar to the length 205 of the spacer 125 between the opposing recesses 220, and the height 227 may be similar to the height 190 of the spacer 125. In various embodiments, the foil stack width 175 is in a range of about 1 mil (about 25 microns) to about 20 mills (about 508 microns). In at least one embodiment, the foil stack width 175 is about 10 mils.

During an exemplary assembly process, the free end side 165 of the foil stack 140 is aligned to the top end portion 210 of two spacers 125, and the length 205 of the spacer is aligned to the length of the foils tack 225. The inner surfaces 180 of the spacers 125 are adjacent the stack surfaces 170, 172. In some embodiments, the inner surfaces 180 are in contact with the stack surfaces 170, 172, directly. In one embodiment, the inner surfaces 180 are in contact with the stack surfaces 170, 172 along the entire length 225 of the foil stack 140, particularly along the top end portion 210 and the free end side 165. The foil stack 140 is compressed by the inner surfaces 180 of the spacers 125 with the greatest height 192 adjacent the inner surface.

The foil stack 140 and spacers 125 may then be coupled via laser beam welding, for example, to form a weld joint 230 (e.g., weld bead) at the free end side 165 of the foil stack 140. With top end portion 210 of the spacers 125 having more mass biased toward the inner surfaces 180 than the outer surfaces 182 and more contact with the foil stack surfaces 170, 172, the free end side 165 of the foil stack 140 may be welded together and with the spacers 125 to form a robust electrical connection without gaps. In addition, the tapered portion 235 reduces excess mass adjacent the weld joint 230 not necessary to form a robust weld joint to facilitate welding with reduced energy and heat dissipation into the plate electrode stack 120.

The welding process may be completed in a single run or multiple runs. The welding process may further round the shapes of the spacers 125 and dissolve the edges of foil tabs 135 in the foil stack 140 in the weld joint 230. The low energy weld and/or the shape of the weld bead may help reduce residual stress in the weld and may enhance mechanical performance.

As shown, the weld joint 230 has a length that is less than the spacer greatest length 205. Moreover, the weld joint 230 length is less than the foil stack length 225. The weld joint 230 has a width that is greater than the foil stack width 175 to join the spacers 125. The weld joint 230 width may include the tapered portions 235 of the spacer top end portions 210 and be less than the width both spacers 125 and the foil stack 140 combined. Furthermore, in some embodiments, the weld joint 230 has a height (e.g., weld depth) that ranges from about 1 mil (about 25 microns) to about 12 mils (about 305 microns).

Thus, embodiments of the POWER TERMINAL FOR IMPLANTABLE DEVICES are disclosed. All references and publications cited herein are expressly incorporated herein by reference in their entirety into this disclosure, except to the extent they may directly contradict this disclosure. Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof. The disclosed embodiments are presented for purposes of illustration and not limitation.

What is claimed is:

1. A battery terminal comprising:
   a foil stack comprising a plurality of free end portions of foil tabs stacked along a stacking direction and electrically coupled to a plurality of plate electrodes, the foil stack defining a free end side, a first stack surface, a second stack surface opposite the first stack surface, and a foil stack width along the stacking direction between the first stack surface and the second stack surface;
   a first side element defining a first inner surface, a first outer surface opposite the first inner surface, a first width between the first inner and outer surfaces, and a first height profile measured between a top and a bottom of the first side element along the first width that reduces in height toward the first outer surface, wherein the first inner surface is coupled to the first stack surface;
   a second side element defining a second inner surface, a second outer surface opposing the second inner surface, a second width between the second inner and outer surfaces, and a second height profile measured between a top and a bottom of the second side element along the second width that reduces in height toward the second outer surface, wherein the second inner surface is coupled to the second stack surface; and
   a weld joint at the free end side of the foil stack coupling the plurality of free end portions, the first side element, and the second side element.

2. The battery terminal of claim 1, wherein the first and second inner surfaces are substantially flat.

3. The battery terminal of claim 1, wherein the first and second inner surfaces are in contact with the first and second stack surfaces, respectively.

4. The battery terminal of claim 3, wherein the first and second stack surfaces define a first and a second foil stack length, wherein the first and second stack surfaces are in contact with the first and second inner surfaces of the first and second side elements along the entire first and second foil stack lengths, respectively.

5. The battery terminal of claim 1, wherein the first and second height profiles define gradual tapers along the first and second widths.

6. The battery terminal of claim 5, wherein the first and second height profiles define curved tapers.

7. The battery terminal of claim 1, wherein the weld joint only partially extends along at least one of a length of the foil stack, the first side element, and the second side element.

8. The battery terminal of claim 1, wherein the first and second side elements each include opposing recesses.

9. The battery terminal of claim 1, wherein the first and second side element comprise at least one of grade 5 titanium and grade 23 titanium.

10. A battery comprising:
    a plate electrode stack comprising a plurality of alternating cathode and anode plate electrodes each bagged in a separator;
    a plurality of cathode foil tabs electrically coupled to the plurality of alternating cathode plate electrodes;
    a plurality of anode foil tabs electrically coupled to the plurality of alternating anode plate electrodes; and
    battery terminals comprising a cathode terminal electrically coupled to the plurality of cathode foil tabs and an anode terminal electrically coupled to the plurality of anode foil tabs, each battery terminal comprising:
       a foil stack comprising a plurality of free end portions of foil tabs stacked along a stacking direction and electrically coupled to a plurality of plate electrodes, the foil stack defining a free end side, a first stack surface, a second stack surface opposite the first stack surface, and a foil stack width along the stacking direction between the first stack surface and the second stack surface;
       a first side element defining a first inner surface, a first outer surface opposite the first inner surface, a first width between the first inner and outer surfaces, and a first height profile measured between a top and a bottom of the first side element along the first width that reduces in height toward the first outer surface, wherein the first inner surface is coupled to the first stack surface;
       a second side element defining a second inner surface, a second outer surface opposing the second inner surface, a second width between the second inner and outer surfaces, and a second height profile measured between a top and a bottom of the second side element along the second width that reduces in height toward the second outer surface, wherein the second inner surface is coupled to the second stack surface; and
       a weld joint at the free end side of the foil stack coupling the plurality of free end portions, the first side element, and the second side element.

11. The battery of claim 10, wherein the first and second inner surfaces are substantially flat.

12. The battery of claim 10, wherein the first and second inner surfaces are in contact with the first and second stack surfaces, respectively.

13. The battery of claim 12, wherein the first and second stack surfaces define a first and a second foil stack length, wherein the first and second stack surfaces are in contact with the first and second inner surfaces of the first and second side elements along the entire first and second foil stack lengths, respectively.

14. The battery of claim 10, wherein the first and second height profiles define tapers along the first and second widths, wherein the tapers narrow from the first and second inner surfaces to the first and second outer surfaces, respectively.

15. The battery of claim 14, wherein the first and second height profiles define curved tapers.

16. The battery of claim 10, wherein the weld joint only partially extends along at least one of a length of the foil stack, the first length, and the second length.

17. The battery of claim 10, wherein the first and second side elements each include opposing recesses.

18. The battery of claim 10, further comprising a cathode pin and an anode pin welded to the first outer surfaces of the cathode and anode terminals, respectively.

19. An implantable medical device comprising:
    stimulation electronics; and
    a battery operatively coupled to the stimulator to power the stimulation electronics, the battery comprising:

a foil stack comprising a plurality of free end portions of foil tabs stacked along a stacking direction and electrically coupled to a plurality of plate electrodes, the foil stack defining a free end side, a first stack surface, a second stack surface opposite the first stack surface, and a foil stack width along the stacking direction between the first stack surface and the second stack surface;

a first side element defining a first inner surface, a first outer surface opposite the first inner surface, a first width between the first inner and outer surfaces, and a first height profile measured between a top and a bottom of the first side element along the first width that reduces in height toward the first outer surface, wherein the first inner surface is coupled to the first stack surface;

a second side element defining a second inner surface, a second outer surface opposing the second inner surface, a second width between the second inner and outer surfaces, and a second height profile measured between a top and a bottom of the second side element along the second width that reduces in height toward the second outer surface, wherein the second inner surface is coupled to the second stack surface; and a weld joint at the free end side of the foil stack coupling the plurality of free end portions, the first side element, and the second side element.

20. The implantable medical device of claim 19, further comprising one or more leads operatively coupled to the stimulation electronics.

* * * * *